(12) United States Patent
West et al.

(10) Patent No.: US 9,962,483 B2
(45) Date of Patent: *May 8, 2018

(54) CASSETTE WITH INFUSION SET CONTAINING ANTI-FREEFLOW BALL VALVE FOR PERISTALTIC INFUSION PUMP

(71) Applicant: NESTEC S.A., Vevey (CH)

(72) Inventors: David Woodruff West, McKinney, TX (US); James Allen Higgins, Plano, TX (US); Seralaathan Hariharesan, Flower Mound, TX (US); Alan P. Halbert, Irving, TX (US)

(73) Assignee: Nestec S.A., Vevey (CH)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/235,928

(22) Filed: Aug. 12, 2016

(65) Prior Publication Data

US 2016/0346464 A1 Dec. 1, 2016

Related U.S. Application Data

(63) Continuation of application No. 13/383,786, filed as application No. PCT/US2010/041312 on Jul. 8, 2010, now Pat. No. 9,440,022.

(Continued)

(51) Int. Cl.
*A61M 39/28* (2006.01)
*F16K 7/06* (2006.01)
*A61M 5/142* (2006.01)

(52) U.S. Cl.
CPC .... *A61M 5/14212* (2013.01); *A61M 5/14232* (2013.01); *A61M 39/281* (2013.01);
(Continued)

(58) Field of Classification Search
CPC .......... F16K 7/063; F16K 7/06; A61M 39/28; A61M 39/284; A61M 39/281; A61M 39/283; A61M 2205/128
(Continued)

(56) References Cited

U.S. PATENT DOCUMENTS

| | | |
|---|---|---|
| 4,142,645 A | 3/1979 | Walton |
| 4,364,266 A | 12/1982 | Williams |

(Continued)

FOREIGN PATENT DOCUMENTS

| | | |
|---|---|---|
| DE | 412088 | 1/1993 |
| EP | 1577187 A1 | 7/2005 |
| WO | 98/05378 | 2/1998 |

OTHER PUBLICATIONS

International Search Report dated Dec. 16, 2010 for corresponding Intl. Appln. No. PCT/2010/041312.
(Continued)

*Primary Examiner* — Mary McManmon
*Assistant Examiner* — Jonathan Waddy
(74) *Attorney, Agent, or Firm* — K&L Gates LLP

(57) ABSTRACT

Flow control devices and methods using the flow control devices are provided. In a general embodiment, a cassette includes a housing having a constrictor, a tube attached to the housing and positioned through the constrictor, and a ball positioned inside the tube. The constrictor can be constructed and arranged to prevent the ball from moving through the tube at the location proximate the constrictor. The ball can prevent fluid flow in one position and be dislodged to allow fluid flow when the cassette is positioned inside a pumping device. As a result, the cassette is designed to prevent free flow of fluid when an enteral feeding tube set is not installed in a pumping device.

18 Claims, 4 Drawing Sheets

Related U.S. Application Data

(60) Provisional application No. 61/225,161, filed on Jul. 13, 2009.

(52) U.S. Cl.
CPC ............. *A61M 39/283* (2013.01); *F16K 7/06* (2013.01); *A61M 2205/128* (2013.01); *Y10T 137/0318* (2015.04); *Y10T 137/8593* (2015.04); *Y10T 137/85978* (2015.04)

(58) Field of Classification Search
USPC ............ 251/4, 5, 7, 8, 9; 417/440, 441, 476, 417/477.2, 479, 480; 604/151, 250
See application file for complete search history.

(56) References Cited

U.S. PATENT DOCUMENTS

| | | | |
|---|---|---|---|
| 4,730,635 A * | 3/1988 | Linden | .................... F16K 7/075 137/1 |
| 5,620,312 A | 4/1997 | Hyman et al. | |
| 5,826,621 A | 10/1998 | Jemmott | |
| 6,523,414 B1 | 2/2003 | Malmstrom et al. | |
| 6,659,976 B2 | 12/2003 | Beck et al. | |
| 6,766,824 B2 | 7/2004 | Taylor | |
| 9,440,022 B2 * | 9/2016 | West | ................. A61M 5/14232 |
| 2002/0151838 A1 | 10/2002 | Beck et al. | |
| 2004/0220542 A1 | 11/2004 | Cise et al. | |

OTHER PUBLICATIONS

Written Opinion dated Jan. 13, 2012 for corresponding Intl. Appl. No. PCT/2010/041312.

* cited by examiner

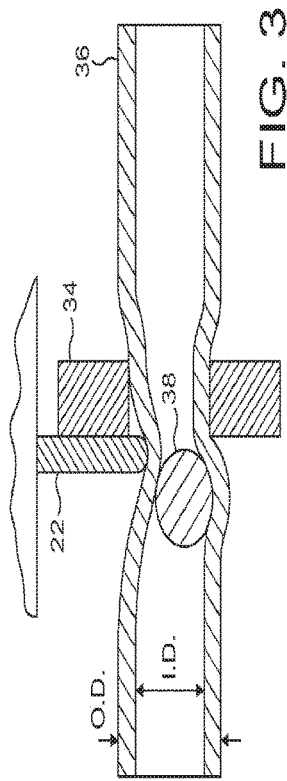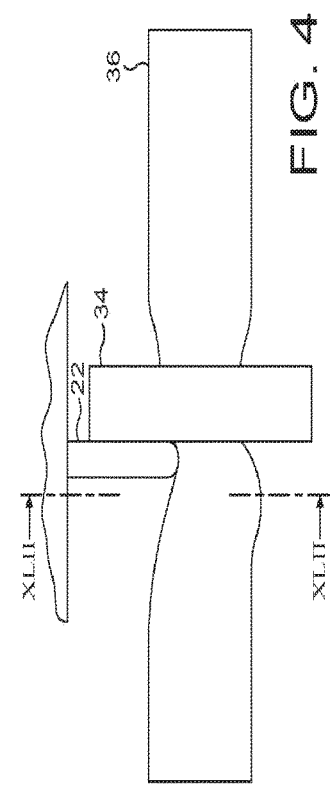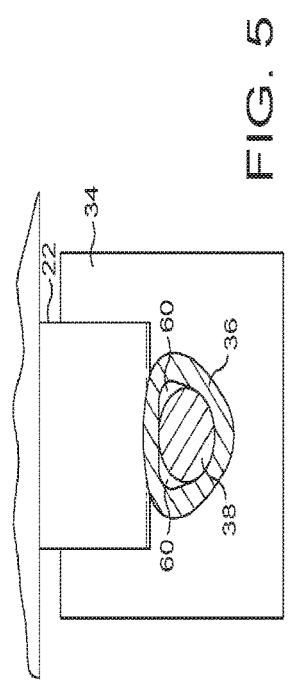

CASSETTE WITH INFUSION SET CONTAINING ANTI-FREEFLOW BALL VALVE FOR PERISTALTIC INFUSION PUMP

PRIORITY CLAIMS

The present application is a continuation of U.S. patent application Ser. No. 13/383,786 filed Apr. 24, 2012, which is a National Stage of International Application No. PCT/US2010/041312 filed Jul. 8, 2010, which claims priority to U.S. Provisional Patent Application Ser. No. 61/225,161, filed on Jul. 13, 2009, the entire contents of which are incorporated herein by reference.

BACKGROUND

The present disclosure generally relates to health and nutrition. More specifically, the present disclosure relates to flow control devices and methods of using the flow control devices.

The delivery of nutritional compositions to mammals, such as human patients, that cannot orally ingest food or other forms of nutrition is often of critical importance. For example, enteral bottles and containers having feeding tubes that deposit food directly into the gastrointestinal tract at a point below the mouth are often used to sustain life while a patient is unable, or refuses, to take food orally. Bottles and containers, feeding tubes and other artificial delivery systems and routes can be used temporarily during the treatment of acute medical conditions. For chronic medical conditions, such systems and routes can be used as part of a treatment regimen that lasts for the remainder of a patient's life. No matter the duration of use, these devices often provide the only means for feeding the patient.

The use of enteral feeding pumps, in conjunction with an enteral feeding tube set as part of an enteral feeding system, for the administering of medical fluids is also well known in the medical arts. The enteral feeding tube set will typically include several long sections of tubing, connected to a centralized, shorter section of tubing. One common concern with the enteral feeding tube set is that fluid flow from a nutritional source through the enteral feeding tube set may begin before the feeding tube set is connected to an enteral administration pump. As a result, the nutritional fluid may spill out of the tube set or be administered to a patient before the desired time.

SUMMARY

The present disclosure relates to flow control devices and methods of using the flow control devices. In a general embodiment, the present disclosure provides a cassette including a housing having a constrictor, a tube attached to the housing and positioned through the constrictor, and a ball located or positioned inside the tube. The constrictor and ball combination can form an "anti-free flow mechanism" in the cassette.

In an embodiment, the tube includes a first end attached to an inlet port and a second end attached to an outlet port. The inlet port can be sized to prevent the ball from entering the inlet port. Any suitable portion of the tube can be flexible. In this regard, the cassette can be part of an enteral feeding tube set that includes tubing connected to the nutritional composition and to a person receiving the nutritional composition along with sensor ports for monitoring fluid flow through the feeding tube set. The cassette is designed to prevent free flow of fluid through the feeding tube set when the feeding tube set is not installed in a pumping device.

In an embodiment, the constrictor is constructed and arranged to prevent the ball from moving through the tube at the location proximate the constrictor. The ball can prevent fluid flow in one position and be dislodged to allow fluid flow when the cassette is positioned inside a pumping device. As a result, the anti-free flow mechanism can be disengaged (e.g. allow fluid flow) for manual priming of the tube set and disengaged when the feeding tube set is installed into a pumping device.

In another embodiment, the present disclosure provides a flow control system including a pumping device having a dislodging mechanism and a cassette removably attached to the pumping device. The cassette includes a housing having a constrictor constructed and arranged to align with the dislodging mechanism when the cassette is positioned within the pumping device. A flexible tube is attached to the housing and positioned through the constrictor, and a ball is positioned inside the flexible tube. The constrictor is constructed and arranged to prevent the ball from moving through the flexible tube at the location proximate the constrictor. The flexible tube can include a first end attached to an inlet port and a second end attached to an outlet port.

In an alternative embodiment, the present disclosure provides a flow control system including a pumping device and a cassette removably attached to the pumping device. The cassette includes a housing having a constrictor and a dislodging mechanism attached at or near the constrictor. A flexible tube is attached to the housing and positioned through the constrictor, and a ball is positioned inside the flexible tube. The constrictor is constructed and arranged to prevent the ball from moving through the flexible tube at the location proximate the constrictor. The flexible tube includes a first end attached to an inlet port and a second end attached to an outlet port.

In yet another embodiment, the present disclosure provides a method of controlling fluid flow in a tube. The method comprises providing a cassette including 1) a housing having a constrictor, 2) a tube attached to the housing and positioned through the constrictor, and 3) a ball positioned inside the tube. Fluid flow is occluded through the tube by positioning the ball within the tube at a location proximate the constrictor. The method further comprises passing fluid through the tube by dislodging the ball within the tube.

In an embodiment, the ball is dislodged when the cassette is positioned inside a pumping device. For example, a dislodging mechanism can be attached to the cassette and constructed and arranged to dislodge the ball when the cassette is positioned inside a pumping device. Alternatively, a dislodging mechanism can be attached within a pumping device and constructed and arranged to dislodge the ball when the cassette is positioned inside a pumping device.

An advantage of the present disclosure is to provide an improved flow control device.

Another advantage of the present disclosure is to provide an improved enteral feeding cassette having an anti-free flow mechanism.

Yet another advantage of the present disclosure is to provide an improved method of preventing fluid flow through an enteral feeding cassette when the cassette is not attached to a pumping device.

Still another advantage of the present disclosure is to provide an improved method of controlling flow during enteral feeding.

Additional features and advantages are described herein, and will be apparent from the following Detailed Description and the figures.

BRIEF DESCRIPTION OF THE FIGURES

FIG. 3 shows a cross-section view of the anti-free flow mechanism shown in FIG. 2.

FIG. 4 shows a partial side view of the anti-free flow mechanism shown in FIG. 2.

FIG. 5 shows a cross-section view V-V of the anti-free flow mechanism shown in FIG. 4.

DETAILED DESCRIPTION

The present disclosure relates to flow control devices and methods of using the flow control devices. In a general embodiment, the present disclosure provides a cassette including a housing having a constrictor, a tube attached to the housing and positioned through the constrictor, and a ball positioned inside the tube. In this configuration, the ball and constrictor combination form the anti-free flow mechanism. The ball restricts fluid flow through the tube when the cassette is not in use. The cassette can be part of an enteral administration device or system that administers nutritional compositions to a person or patient in need of same.

The cassette that houses the anti-free flow mechanism provides the user an elegant way to install the anti-free flow mechanism and feeding tube set into a pumping device via features built into a housing of the cassette and also provides other built in functionality (sensor ports, etc.) for successful delivery of the nutritional composition to a person or patient. The anti-free flow mechanism prevents leakage/flow of the nutritional composition in the enteral feeding tube set, for example, in the following instances: 1) before and after the feeding tube set is primed with the feeding fluid, 2) during the loading and unloading of the feeding tube set into and out of the pumping device and 3) after the feeding tube set has been removed from the pumping device.

As used herein, the term "nutritional composition" includes, but is not limited to, complete nutritional compositions, partial or incomplete nutritional compositions, and disease or condition specific nutritional compositions. A complete nutritional composition (i.e. those which contain all the essential macro and micro nutrients) can be used as a sole source of nutrition for the patient. Patients can receive 100% of their nutritional requirements from such complete nutritional composition. A partial or incomplete nutritional composition does not contain all the essential macro and micro nutrients and cannot be used as a sole source of nutrition for the patient. Partial or incomplete nutritional compositions can be used as nutritional supplements.

Figure 1:
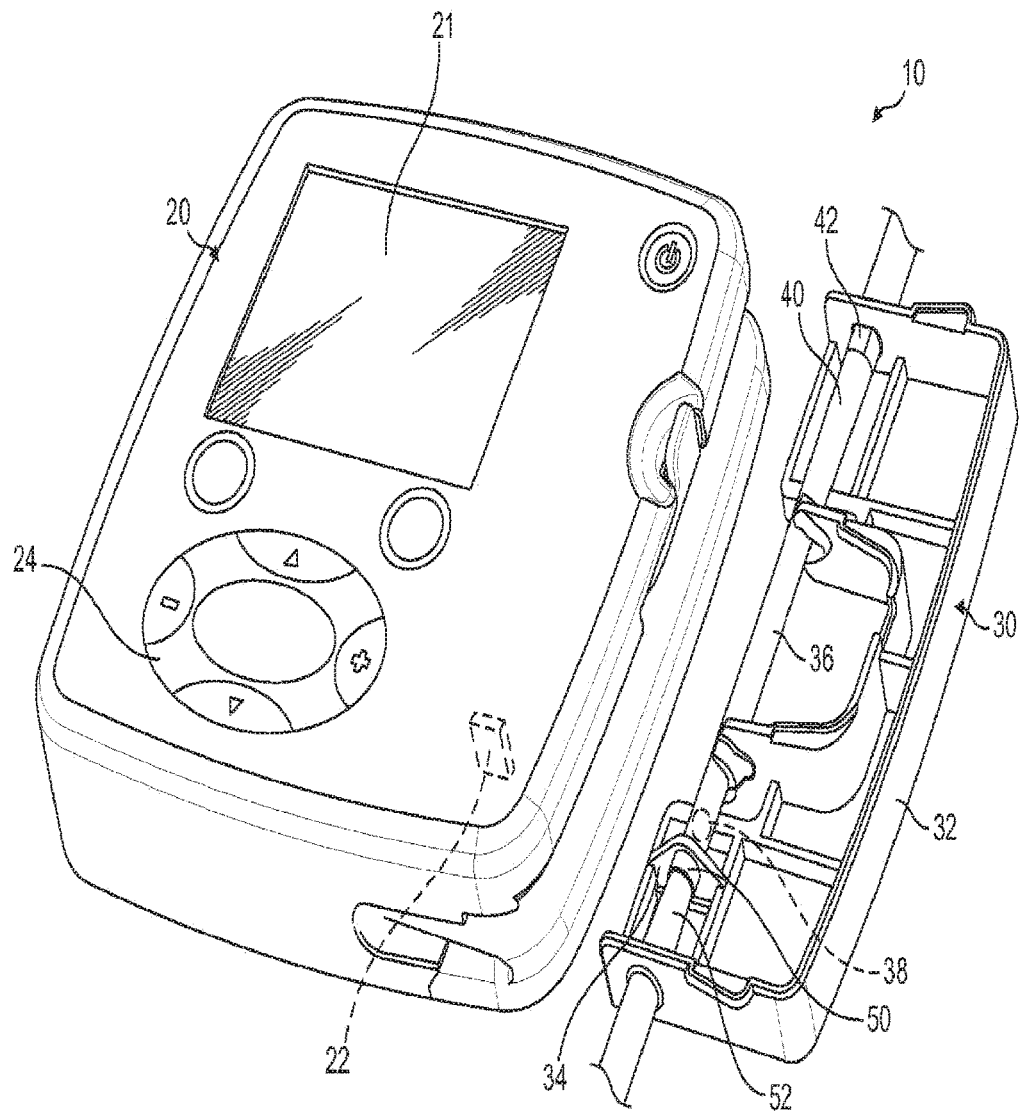
FIG. 1 shows a pumping device and a cassette having an anti-free flow mechanism in an embodiment of the present disclosure.
Figure 2:
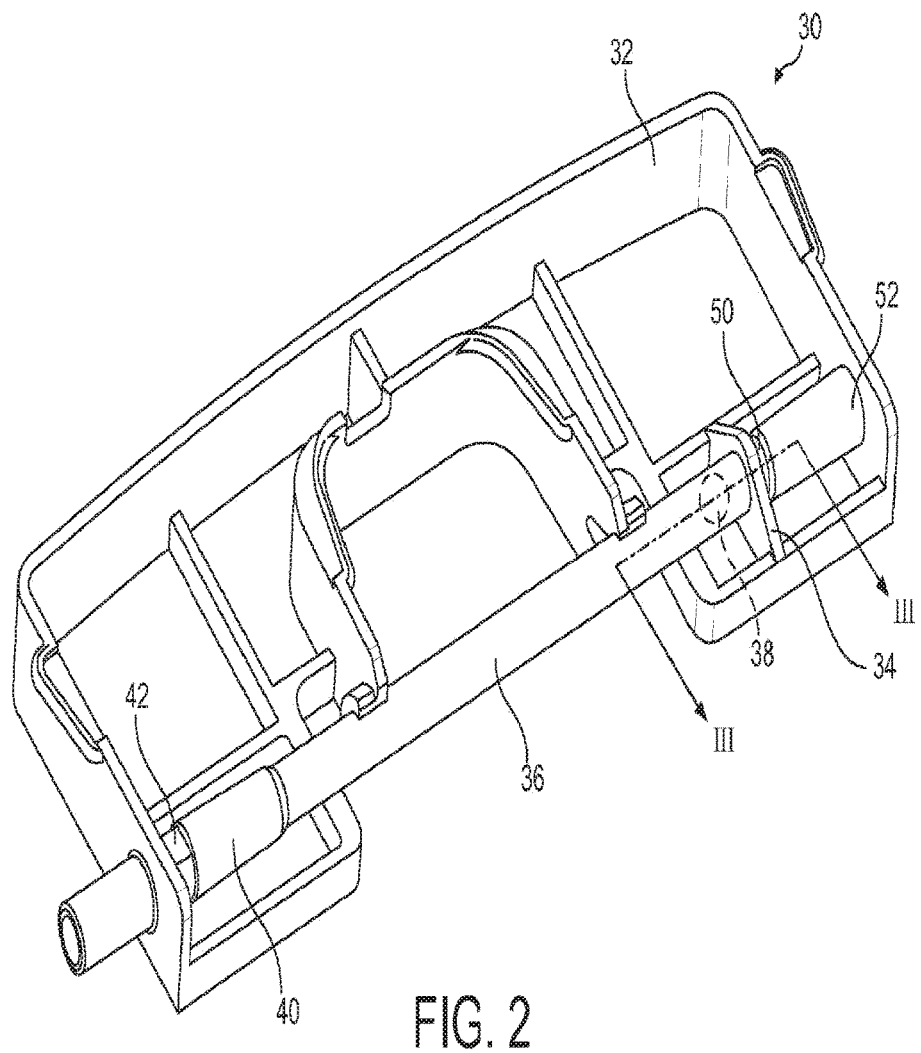
FIG. 2 shows a cassette having an anti-free flow mechanism in an embodiment of the present disclosure.

In an embodiment illustrated in FIGS. 1-2, the present disclosure provides a flow control system 10 including a pumping device 20 having a dislodging mechanism 22. Flow control system 10 further includes a cassette 30 removably attached to pumping device 20. The design of cassette 30 can help in loading an enteral feeding tube set (not shown) into pumping device 20 without having to route/guide the tubes or stretch the tubes from the tube set over a rotor (e.g. part of a peristaltic pump).

Pumping device 20 can be an enteral feeding pump. Non-limiting examples of pumping devices are described in U.S. Pat. No. 6,659,976, which is incorporated herein by reference. Pumping device 20 can include a monitor/information screen 21 and a control pad 24 for operating pumping device 20.

Cassette 30 can have any suitable shape such as the one shown in FIGS. 1-2 and is design to be positioned within pumping device 20. Non-limiting examples of alternative cassette configurations are described in U.S. Pat. Nos. D504,506, D505,199, D455,489, D501,924 and D507,647, which are incorporated herein by reference. Cassette 30 can be made from any suitable rigid, semi-rigid or flexible material. Cassette 30 can also be "keyed/poka yoked" such that it can be inserted into pumping device 20 only one way.

As illustrated in FIGS. 1-2, cassette 30 includes a housing 32 having a constrictor 34 constructed and arranged to align with dislodging mechanism 22 of pumping device 20 when cassette 30 is positioned within pumping device 20. A flexible tube 36 is attached to housing 32 and positioned through constrictor 34. Flexible tube 36 can be made of any suitable materials such as silicone. It should be appreciated that any suitable portion of flexible tube 36 can be flexible while the remaining portion is rigid or semi-rigid.

A ball 38 is located or positioned inside flexible tube 36. Constrictor 34 is constructed and arranged to prevent ball 38 from moving through flexible tube 36 at the location proximate constrictor 34. For example, constrictor 34 can define a hole or passage that is slightly smaller than the outside diameter ("OD") of flexible tube 36 that is assembled in cassette 30 as seen in FIG. 3. It should be appreciated that ball 38 can have any suitable shape (e.g. spherical, cube, polygonal) to match the inner diameter ("ID") shape of the passageway of flexible tube 36.

Flexible tube 36 can include a first end 40 attached to an inlet port 42 and a second end 50 attached to an outlet port 52. As a result, fluid can flow through flexible tube 36 in the direction from first end 40 to second end 50. Inlet port 42 can be attached to a tube connected to a nutritional composition source. Outlet port 52 can be attached to a tube connected to the person receiving the nutrition composition.

In alternative embodiments, inlet port 42 and outlet port 52 can include upstream and downstream occlusion detection sensors (not shown), respectively. The term "upstream" refers to the section of the tube between a nutritional composition source (e.g. feed bag) and a pump rotor (e.g peristaltic pump) used to provide fluid flow. The term "downstream" refers to the section of the tube between the pump rotor and a distal end connector to a person receiving the nutritional composition.

Cassette 20 can include sensor ports and sensor windows built-in. For example, the shape and size of the ports and windows can work uniquely with the sensors in the pumping device to detect upstream and downstream occlusion and/or to detect air in the fluid flow line or tubing. In addition, any portion of cassette 30 can incorporate other features to prevent cassette 30 from being incorrectly inserted into pumping device 20.

During operation, when flexible tube 36 is inserted into constrictor 34, flexible tube's 36 OD will conform to the size of the hole of constrictor 34 and proportionally reduce the ID of flexible tube 36. Ball 38 is placed inside flexible tube 36 of cassette 30, directly in the flow path of the fluid and in the upstream side of the constrictor 34 (see FIG. 3). Ball 38 is sized such that, it is larger than the reduced ID of flexible tube 36 at the location proximate constrictor 34.

When a fluid in flexible tube 36 is under pressure, ball 38 will be pushed towards and against constrictor 34 (see FIG. 3). Because ball 38 is larger than the reduced ID of flexible tube 36 at constrictor 34, ball 38 will squeeze flexible tube 36 against the surface of constrictor 34. As a result, the tube material between ball 38 and constrictor 34 acts as a gasket or o-ring to prevent ball 38 from passing through constrictor 34.

The fluid pressure acting on ball 38 forces ball 38 against the gasket formed and occludes the fluid flow path through flexible tube 36. With increasing pressure, the sealing force on ball 38 increases proportionally thereby creating a much better seal to prevent fluid flow.

To un-occlude or allow fluid flow through flexible tube 36, ball 38 is mechanically dislodged by dislodging mechanism 22, which can be incorporated in pumping device 20 as shown in FIGS. 1 and 3-5. As seen in FIGS. 3-5, dislodging mechanism 22 will push on the outer surface of flexible tube 36 and dislocate ball 38 by moving ball 38 out of its seated/sealing position. Once ball 38 is dislocated/dislodged, the flow path is open and fluid will flow through flexible tube 36 through newly formed voids 60 due to the distortion of the ID of flexible tube 36.

On removal of dislodging mechanism 22 (e.g. by removing cassette 30 from pumping device 20), ball 38 will reseat itself (due to the elasticity of flexible tube 38 and the fluid pressure that acts on it) in constrictor 34 and seal the flow path once again (see FIG. 3). As a result, the anti-free flow mechanism can be unlocked and deactivated by pump 20 when cassette 30 is inserted and reactivated when it is removed from pump 20. Unlike conventional anti-free flow devices in existing enteral feeding tube sets, cassette 30 is not deactivated by closing a door, by pressure, or a roller clamp. Instead, it will be deactivated by physically dislodging ball 38 via a feature in pumping device 20.

In sum, the anti-free flow mechanism inside cassette 30 can be activated by pressure and deactivated via mechanically displacing ball 38. No spring is required in the system to activate the anti-free flow mechanism. Pressure acting on ball 38 will seal the flow path thereby preventing flow through flexible tube 36. This anti-free flow mechanism prevents any static pressure loss during pumping. When cassette 30 is inside pumping device 20, the flow can be prevented/controlled by pump rollers (e.g. peristaltic pumps) within pumping device 20.

Figure 6:
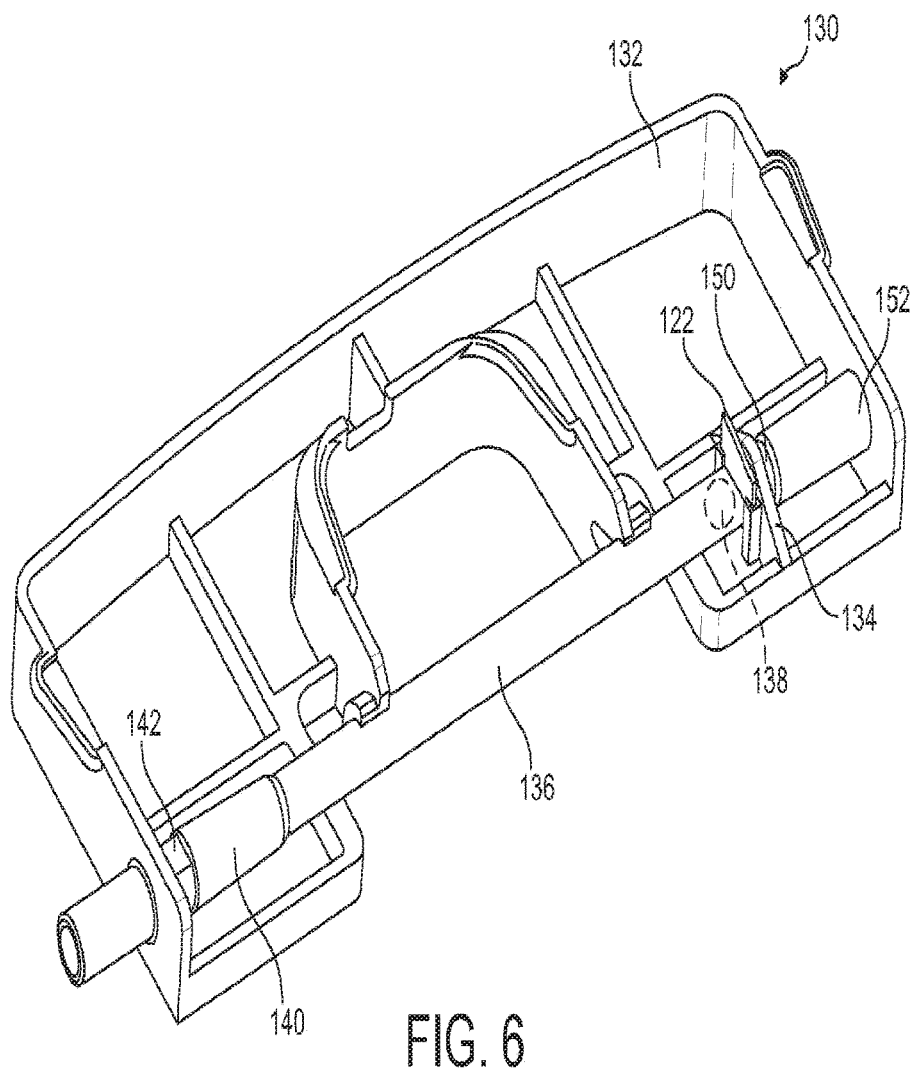
FIG. 6 shows a cassette having an anti-free flow mechanism in another embodiment of the present disclosure.

In an alternative embodiment illustrated in FIG. 6, the present disclosure provides a cassette 130 including a housing 132 having a constrictor 134 and a dislodging mechanism 122 movably attached at or near constrictor 134. A flexible tube 136 is attached to housing 132 and positioned through constrictor 134. A ball 138 is positioned inside flexible tube 136. Constrictor 134 is constructed and arranged to prevent ball 138 from moving through flexible tube 136 at the location proximate constrictor 134. Flexible tube 136 can include a first end 140 attached to an inlet port 142 and a second end 150 attached to an outlet port 152. Cassette 130 can be removably attached to any suitable pumping device.

A pumping device compatible with cassette 130 does not need to include any dislodging mechanism. In this regard, when cassette 130 is inserted into the pumping device, a surface of the pumping device can push down on dislodging member 122 into flexible tube 136 and cause dislodging member 122 to dislodge or move ball 138 from its position at or near constrictor 134. As a result of the distortion of flexible tube 136, fluid can flow past ball 138. When cassette 130 is removed from the pumping device, flexible tube 136 can reform to its original shape thereby allowing ball 138 to be re-positioned at or near constrictor 134 and block flow in flexible tube 136.

In yet another embodiment, the present disclosure provides a method of controlling fluid flow in a tube. The method includes providing a cassette including 1) a housing having a constrictor, 2) a tube attached to the housing and positioned through the constrictor, and 3) a ball positioned inside the tube. Fluid flow is occluded through the tube by positioning the ball within the tube at a location proximate the constrictor. The method further includes passing fluid through the tube by dislodging the ball within the tube.

In an embodiment, the ball is dislodged when the cassette is positioned inside a pumping device. For example, a dislodging mechanism can be attached to the cassette and constructed and arranged to dislodge the ball when the cassette is positioned inside a pumping device. Alternatively, a dislodging mechanism can be attached within a pumping device and constructed and arranged to dislodge the ball when the cassette is positioned inside a pumping device.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A method of controlling fluid flow in a flexible tube, the method comprising:
   providing a cassette for being connected to a pumping device, wherein the cassette comprises a housing having a constrictor, the flexible tube attached to the housing and positioned through the constrictor such that an inner diameter (ID) of the flexible tube is reduced, and a ball positioned inside the flexible tube;
   occluding fluid flow through the flexible tube by positioning the ball within the flexible tube at an upstream side of the constrictor when the flexible tube is positioned through the constrictor; and
   passing fluid through the flexible tube by mechanically dislodging the ball to move the ball within the flexible tube in a direction along a main extension direction of the flexible tube, wherein, when the ball is not dislodged, the ball sealingly seats against the flexible tube at the constrictor to prevent fluid flow through the flexible tube.

2. The method of claim 1, wherein the ball is dislodged when the cassette is positioned inside the pumping device.

3. The method of claim 1, wherein a dislodging mechanism is attached to the cassette and is configured to dislodge the ball when the cassette is positioned inside the pumping device.

4. The method of claim 3, wherein the ball and the flexible tube are configured such that the ball can reseat itself upon removal of the dislodging mechanism when fluid pressure acts on the ball.

5. A cassette for being connected to a pumping device, the cassette comprising:
   a housing comprising a constrictor;
   a flexible tube attached to the housing and positioned through the constrictor such that an inner diameter (ID) of the flexible tube is reduced;

a ball positioned inside the flexible tube at an upstream side of the constrictor, the ball being sized such that the ball is larger than the reduced inner diameter (ID) of the flexible tube at the constrictor such that the ball can prevent the fluid from flowing through the flexible tube when the flexible tube is positioned through the constrictor; and a dislodging mechanism configured to mechanically dislodge the ball to move the ball in a direction along a main extension direction of the flexible tube to allow the fluid to flow through the flexible tube, wherein, when the dislodging mechanism does not dislodge the ball, the ball is configured to sealingly seat against the flexible tube at the constrictor to prevent fluid flow through the flexible tube.

6. The cassette of claim 5, wherein the constrictor is configured to prevent the ball from moving through the tube at a location proximate the constrictor.

7. The cassette of claim 5, wherein the tube comprises a first end attached to an inlet port and a second end attached to an outlet port.

8. The cassette of claim 5, wherein an inlet port is sized to prevent the ball from entering the inlet port.

9. The cassette of claim 5, wherein the ball is configured to squeeze a portion of the flexible tube against the constrictor when a fluid pressure acts on the ball such that the ball seats in a sealing position against the flexible tube at the constrictor.

10. The cassette of claim 9, wherein the dislodging mechanism is arranged to push on an outer surface of the flexible tube to dislocate the ball by moving the ball out of the sealing position.

11. The cassette of claim 5, wherein the ball is configured such that a sealing force of the ball increases proportionally to the fluid pressure acting on the ball.

12. The cassette of claim 5, wherein the dislodging mechanism is configured to mechanically dislodge the ball when the cassette is connected to the pumping device.

13. The cassette of claim 5, wherein the dislodging mechanism is configured to align with the constrictor.

14. The cassette of claim 5, wherein the dislodging mechanism comprises a plate configured to extend at least partially across the flexible tube and along a plane perpendicular to the main extension direction of the flexible tube.

15. A cassette assembly for cooperating with a pumping device, the cassette assembly comprising:

a housing comprising a constrictor;

a flexible tube attached to the housing and positioned through the constrictor such that an inner diameter of the flexible tube is reduced;

a ball positioned inside the flexible tube at an upstream side of the constrictor, the ball being sized such that the ball is larger than the reduced inner diameter of the flexible tube at the constrictor such that the ball prevents the fluid from flowing through the flexible tube when the flexible tube is positioned through the constrictor; and a dislodging mechanism configured to mechanically dislodge the ball to move the ball in a direction along a main extension direction of the flexible tube to allow the fluid to flow through the flexible tube, wherein, when the dislodging mechanism does not dislodge the ball, the ball is configured to sealingly seat against the flexible tube at the constrictor to prevent fluid flow through the flexible tube.

16. The cassette assembly of claim 15, wherein the ball is configured to squeeze a portion of the flexible tube against the constrictor when a fluid pressure acts on the ball such that the ball seats in a sealing position against the flexible tube at the constrictor.

17. The cassette assembly of claim 15, wherein the dislodging mechanism is configured to align with the constrictor.

18. The cassette assembly of claim 15, wherein the dislodging mechanism comprises a plate configured to extend at least partially across the flexible tube and along a plane perpendicular to the main extension direction of the flexible tube.

* * * * *